(12) United States Patent
Taniuchi et al.

(10) Patent No.: US 10,099,221 B2
(45) Date of Patent: Oct. 16, 2018

(54) COLUMN ATTACHMENT DEVICE

(71) Applicant: Shimadzu Corporation, Kyoto (JP)

(72) Inventors: Hirokazu Taniuchi, Kyoto (JP); Hajime Takemoto, Kyoto (JP); Shoji Ide, Kyoto (JP); Yasunori Terai, Kyoto (JP); Ryo Takechi, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 176 days.

(21) Appl. No.: 15/311,584

(22) PCT Filed: May 16, 2014

(86) PCT No.: PCT/JP2014/063030
§ 371 (c)(1),
(2) Date: Nov. 16, 2016

(87) PCT Pub. No.: WO2015/173944
PCT Pub. Date: Nov. 19, 2015

(65) Prior Publication Data
US 2017/0120251 A1 May 4, 2017

(51) Int. Cl.
*B01L 9/00* (2006.01)
*G01N 30/60* (2006.01)
*B01D 53/02* (2006.01)
*G01N 30/02* (2006.01)

(52) U.S. Cl.
CPC ............. *B01L 9/50* (2013.01); *B01D 53/025* (2013.01); *G01N 30/6004* (2013.01); *G01N 30/6026* (2013.01); *G01N 30/6047* (2013.01); *G01N 2030/025* (2013.01)

(58) Field of Classification Search
CPC .. B01L 9/50; G01N 30/6004; G01N 30/6026; G01N 30/6047; G01N 2030/025; B01D 53/025
See application file for complete search history.

(56) References Cited

U.S. PATENT DOCUMENTS

| 4,991,883 A * | 2/1991 | Worden | B01J 4/001 |
| | | | 285/334.4 |
| 5,234,235 A * | 8/1993 | Worden | F16L 29/04 |
| | | | 285/334.4 |
| 8,128,131 B2 | 3/2012 | Barnett et al. | |
| 2017/0227507 A1 * | 8/2017 | Brann | G01N 30/6004 |

* cited by examiner

Primary Examiner — Robert Clemente
(74) Attorney, Agent, or Firm — Muir Patent Law, PLLC

(57) ABSTRACT

A ferrule 10 is pressed by a pressing plate 35, and the ferrule 10 is thereby sandwiched and fixed between a ferrule receiving part 20 and ferrule pressing part 30. The pressing plate 35 is displaced by a displacing mechanism 350, whereby the pressing plate 35 is switched between a contacting state in which the pressing plate 35 is in contact with the ferrule 10 and a non-contacting state in which the pressing plate 35 is not in contact with the ferrule 10 and the ferrule 10 can pass thorough the inside of the ferrule pressing part 30. By displacement of the pressing plate 35 to the non-contacting state, the ferrule pressing part 30 can be extracted from the ferrule 10 side, and the ferrule pressing part 30 can therefore be removed from a column 2 in a state in which the ferrule 10 is attached in a swaged fashion.

5 Claims, 16 Drawing Sheets

COLUMN ATTACHMENT DEVICE

TECHNICAL FIELD

The present invention relates to a column attachment device for attaching a column to an attachment position.

BACKGROUND ART

In a gas chromatograph, a carrier gas is introduced into a column from a sample introduction part together with a sample, and each sample component is separated while the carrier gas passes through the column. Each sample component separated in the column is detected by a detector connected to the column. The connection of the column to a sample introduction part or a detector can be performed via a column attachment device.

The column attachment device is provided with, for example, a ferrule, a ferrule receiving part, and a ferrule pressing part. The ferrule is attached to the column by being swaged in a state in which the column is inserted. And, by fixing the ferrule attached to the column by pinching between the ferrule receiving part and the ferrule pressing part, the column can be attached to the column attachment device (see, for example, the following Patent Document 1).

In a conventional column attachment device as exemplified by Patent Document 1, a ferrule pressing part is screwed in the ferrule receiving part and attached thereto. Concretely, screw threads are formed on the inner peripheral surface of the cylindrical ferrule receiving part, and screw grooves are formed on the outer peripheral surface of the tip end part of the ferrule pressing part to be screwed in the ferrule receiving part.

FIGS. 10A to 10C are schematic cross-sectional views for explaining an attachment work flow of a column 101. As shown in FIG. 10A, initially, a column 101 is inserted into a ferrule pressing part 102, so that it is set to a state in which the tip end part of the column 101 is protruded from the ferrule pressing part 102. Thereafter, as shown in FIG. 10B, the ferrule 103 is inserted into the tip end part of the column 101 and the positioning of the column 101 to the ferrule 103 is performed. Then, the ferrule 103 is swaged.

As described above, after the ferrule 103 is attached to the column 101, as shown in FIG. 10C, the ferrule pressing part 102 is screwed in the ferrule receiving part 104, so that the ferrule 103 is fixed between the ferrule receiving part 104 and the ferrule pressing part 102. The ferrule receiving part 104 is attached to a sample introduction part or a detector which is a connection target of the column 101.

PRIOR ART DOCUMENT

Patent Document

Patent Document 1: U.S. Pat. No. 8,128,131

SUMMARY OF THE INVENTION

Problems to be Solved by the Invention

When an analysis is not performed, the ferrule pressing part 102 is removed from the ferrule receiving part 104, so that the column 101 is removed from the sample introduction part or the detector. At this time, in the aforementioned conventional column attachment device, there is a problem that the ferrule pressing part 102 cannot be removed from the column 101 and therefore the ferrule pressing part 102 should be stored together with the column 101.

That is, as shown in FIG. 10B, the ferrule 103 is swagedly attached to the tip end part of the column 101 in a state in which the tip end part is inserted in the ferrule pressing part 102. Therefore, even in cases where it is attempted to pull out the ferrule pressing part 102 toward the ferrule 103 side (upper side in FIG. 10B), the ferrule 103 gets caught on the ferrule pressing part 102, which prevents removal of the ferrule pressing part 102. Further, even in cases where it is attempted to pull out the ferrule pressing part 102 toward the opposite side (lower side in FIG. 10B) of the ferrule 103 side, the column 101 wound in a loop shape becomes an obstacle, which prevents removal of the ferrule pressing part 102.

The present invention was made in view of the aforementioned circumstances, and aims to provide a column attachment device capable of removing a ferrule pressing part from a column in a state in which the ferrule is swagedly attached to the column.

Means for Solving the Problems

A column attachment device according to the present invention is a column attachment device for attaching a column to an attachment position, and is provided with a ferrule, a ferrule receiving part, and a ferrule pressing part. The ferrule is attached to the column by being inserted by the column and swaged at one end part side of the ferrule. The ferrule receiving part receives one end part side of the ferrule. The ferrule pressing part is attached to the ferrule receiving part and fixes the ferrule by pinching the ferrule between the ferrule pressing part and the ferrule receiving part by pressing the ferrule from the other end part side toward the ferrule receiving part side. The ferrule pressing part includes a pressing plate and a displacing mechanism. The pressing plate presses the ferrule. The displacing mechanism displaces the pressing plate to thereby switch the pressing plate between a contacting state in which the pressing plate is in contact with the ferrule and a non-contacting state in which the pressing plate is not in contact with the ferrule and the ferrule can pass thorough the inside of the ferrule pressing part.

With this configuration, by displacing the pressing plate to thereby switch the pressing plate to the non-contacting state, it becomes possible for the ferrule to pass through the inside of the ferrule pressing part, and therefore the ferrule pressing part can be extracted from the ferrule side. Therefore, the ferrule pressing part can be removed from the column in a state in which the ferrule is swagedly attached to the column. Further, by displacing the pressing plate to switch the pressing plate to the contacting state, the ferrule is pressed by the pressing plate toward the ferrule receiving part side, and therefore the ferrule can be assuredly fixed between the ferrule receiving part and the ferrule pressing part.

It is preferable that the ferrule pressing part include an urging member for urging the ferrule toward the ferrule receiving part side via the pressing plate when the pressing plate is in the contacting state.

With this structure, the ferrule can be pressed toward the ferrule receiving part side by a sufficient pressing force with the urging force of the urging member. Especially, since the urging force of the urging member acts on the ferrule via the pressing plate, rattling of the pressing plate can be prevented. Further, by the urging force of the urging member, the pressing plate can be stably held in the contacting state or the non-contacting state.

The displacing mechanism may be provided with a shaft portion that rotatably supports each pressing plate. In this case, it may be configured such that the pressing plate is switched between the contacting state and the non-contacting state by a rotation of the pressing plate centering on the shaft portion.

According to such a configuration, with a simple configuration of simply rotating the pressing plate centering on the shaft portion, the pressing plate can be switched between the contacting state and the non-contacting state. In this case, in cases where the operation portion to be operated by an operator is provided at the pressing plate and the operation portion is protruded from the ferrule pressing part, with a more simple configuration of simply operating the operation portion, the pressing plate can be switched between the contacting state and the non-contacting state.

The displacing mechanism may be provided with a plurality of pressing plates and a plurality of shaft portions rotatably supporting each pressing plate, and a rotary plate provided with the plurality of shaft portions. In this case, it may be configured such that the rotary plate is rotated to simultaneously rotate the plurality of pressing plates, so that the pressing plate is switched between the contacting state and the non-contacting state.

With such as configuration, by rotating the rotary plate to thereby simultaneously rotate the plurality of pressing plates, the pressing plates can be switched between the contacting state and the non-contacting state. In this case, in cases where the rotary plate is composed of a circular plate provided coaxially with the center axis line of the ferrule pressing part and the rotary plate is rotated centering on the center axis line, so that the plurality of pressing plates are rotated simultaneously, with a simple configuration of simply rotating the circular plate, the pressing plate can be switched between the contacting state and the non-contacting state.

The displacing mechanism may be provided with a guide portion that slidably holds the pressing plate. In this case, it may be configured such that the pressing plate is switched between the contacting state and the non-contacting state by sliding of the pressing plate.

According to such a configuration, with a simple configuration of simply slidably moving the pressing plate, the pressing plate can be switched between the contacting state and the non-contacting state. In this case, in cases where the operation portion to be operated by an operator is provided at the pressing plate and the operation portion is protruded from the ferrule pressing part, with a more simple configuration of simply operating the operation portion, the pressing plate can be switched between the contacting state and the non-contacting state.

Effects of the Invention

According to the present invention, by displacing the pressing plate to switch the pressing plate to the non-contacting state, the ferrule pressing part can be extracted from the ferrule side, and therefore the ferrule pressing part can therefore be removed from a column in a state in which the ferrule is attached in a swaged fashion.

EMBODIMENTS FOR CARRYING OUT THE INVENTION

Figure 1:
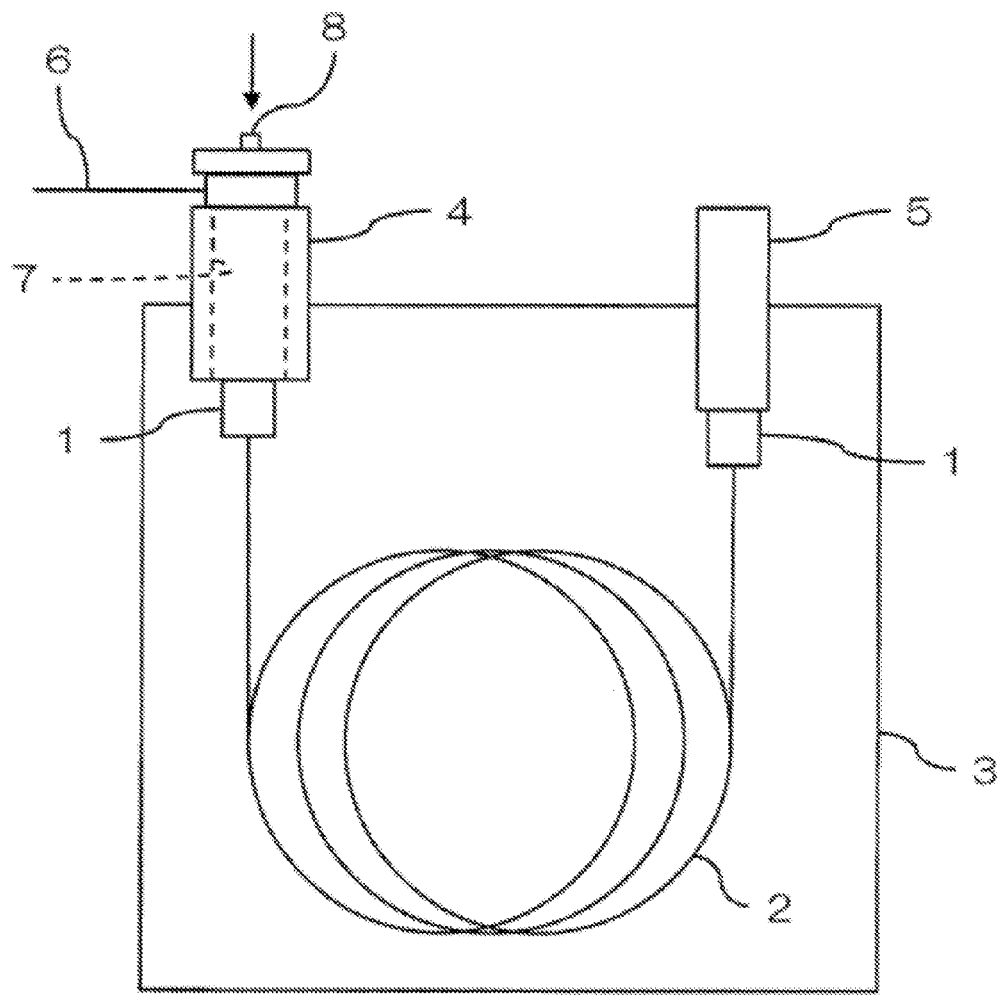
FIG. 1 is a schematic view showing a configuration example of a gas chromatograph to which a column attachment device according to a first embodiment of the present invention is applied.

FIG. 1 is a schematic view showing a configuration example of a gas chromatograph to which a column attachment device according to a first embodiment of the present invention is applied. This gas chromatograph is used for performing an analysis by supplying a carrier gas together with a sample to the inside of the column 2, and is equipped with, in addition to the aforementioned column attachment device 1 and the column 2, a column oven 3, a sample introduction part 4, a detector 5, etc.

The column 2 is composed of, for example, a capillary column, and is heated in the column oven 3 during the analysis. The carrier gas is supplied to the inside of the column 2 from the sample introduction part 4 together with a sample. Each sample component is separated in the course of passing through the column 2 and detected by a detector 5. The detector 5 can be configured by various detectors, such as, e.g., a hydrogen flame ionization detector (FID).

The sample introduction part 4 is used to introduce a sample to the inside of the column 2 together with a carrier gas supplied from the carrier gas supply path 6, and is provided with, for example, a vaporization chamber 7 therein. A liquid sample is introduced to the sample vaporization chamber 7 from the sample inlet 8, and the sample vaporized in the sample vaporization chamber 7 is introduced to the inside of the column 2 together with the carrier gas.

The column attachment device 1 connects one end portion of the column 2 to the sample introduction part 4, and also connects the other end portion of the column 2 to the detector 5. In this embodiment, the following description will be directed to the case in which the column attachment device 1 that connects one end portion of the column 2 to the sample introduction part 4 and the column attachment device 1 that connects the other end portion of the column 2 to the detector 5 are the same in structure. However, they may be different in structure.

Figure 2:
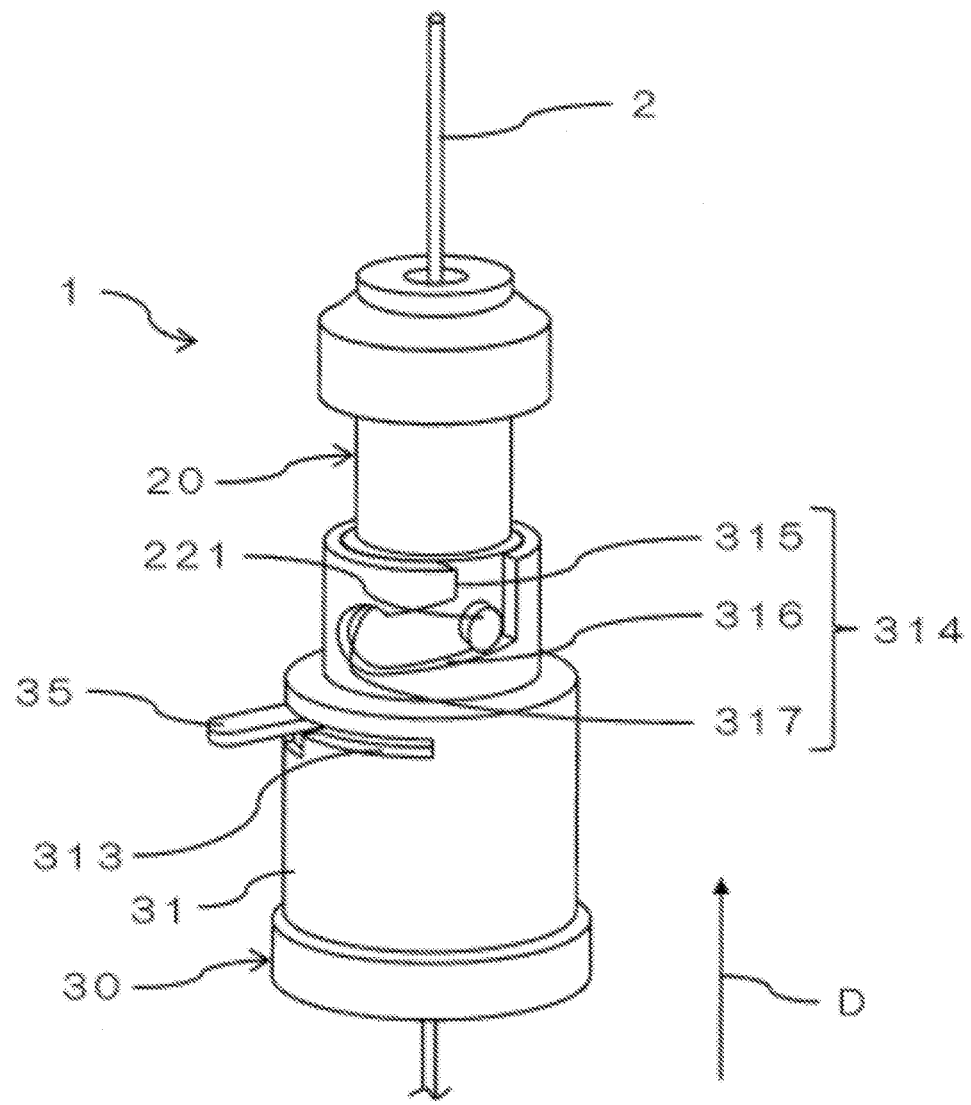
FIG. 2 is a perspective view showing a configuration example of the column attachment device.
Figure 3:
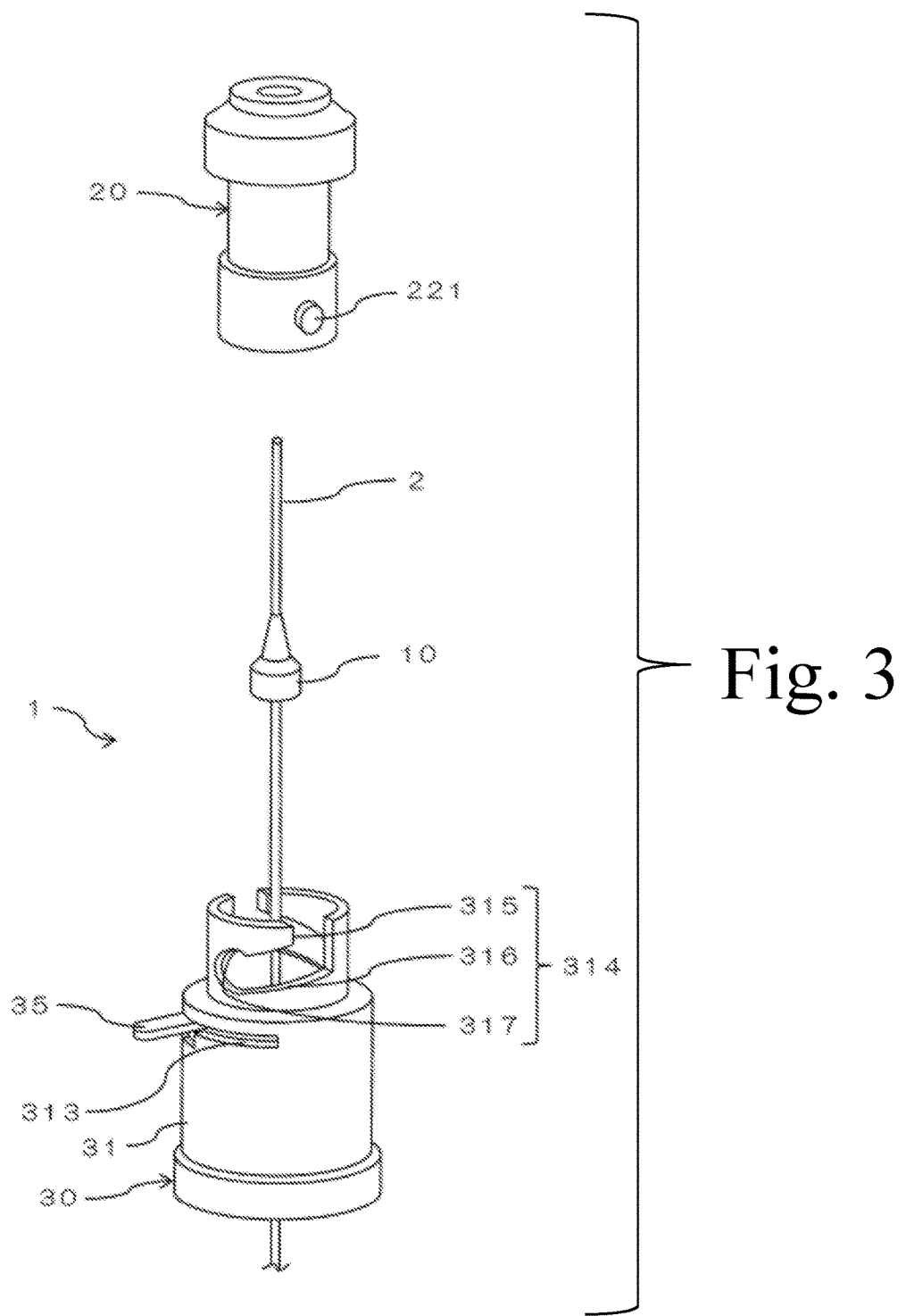
FIG. 3 is an exploded perspective view of the column attachment device shown in FIG. 2.

FIG. 2 is a perspective view showing a configuration example of the column attachment device 1. Further, FIG. 3 is an exploded perspective view of the column attachment device 1 shown in FIG. 2. The column attachment device 1 is a device for attaching a column 2 to an attachment position of the sample introduction part 4, the detector 5, etc., and is equipped with a ferrule 10, a ferrule receiving part 20, and a ferrule pressing part 30.

The ferrule 10 is a cylindrical member in which one end part side thereof is formed into a tapered shape, and a column 2 is inserted to the inside of the ferrule. As the ferrule 10, for example, a metallic ferrule is used, but not limited to it. The ferrule may be made of resin, etc. As shown in FIG. 3, the column 2 is inserted to the inside of the ferrule pressing part 30, so that it is set to a state in which the tip end part of the column is protruded from the ferrule pressing part 30. Thereafter, a ferrule 10 is inserted to the tip end part of the column 2, and one end part side of the ferrule 10 is swaged. Thus, the ferrule 10 is attached to the column 2. In this disclosure, the wording "swage" denotes a work for plastically deforming the ferrule 10 by applying a pressure to be performed as a temporary tightening before final tightening which is a work for fixing the column 2 to an attachment position.

The ferrule receiving part 20 receives one end part side of the ferrule 10 at the time of final tightening. At the time of final tightening, as shown in FIG. 2, the ferrule pressing part 30 is attached to the ferrule receiving part 20, so that the ferrule 10 is pressed from the other end part side toward the ferrule receiving part 20 side. Thus, the ferrule 10 is pinched between the ferrule receiving part 20 and the ferrule pressing part 30 to be fixed.

In this embodiment, a pressing plate 35 configured to press the ferrule 10 toward the ferrule receiving part 20 side which comes into contact with the other end part side of the ferrule 10 at the time of final tightening is provided at the ferrule pressing part 30 in a displaceable manner. The pressing plate 35 is configured to be displaceable between a contact state in which the pressing plate 35 is in contact with the other end part side of the ferrule 10 and a non-contacting state in which the pressing plate 35 is not in contact with the other end part side of the ferrule 10.

Figure 4A:
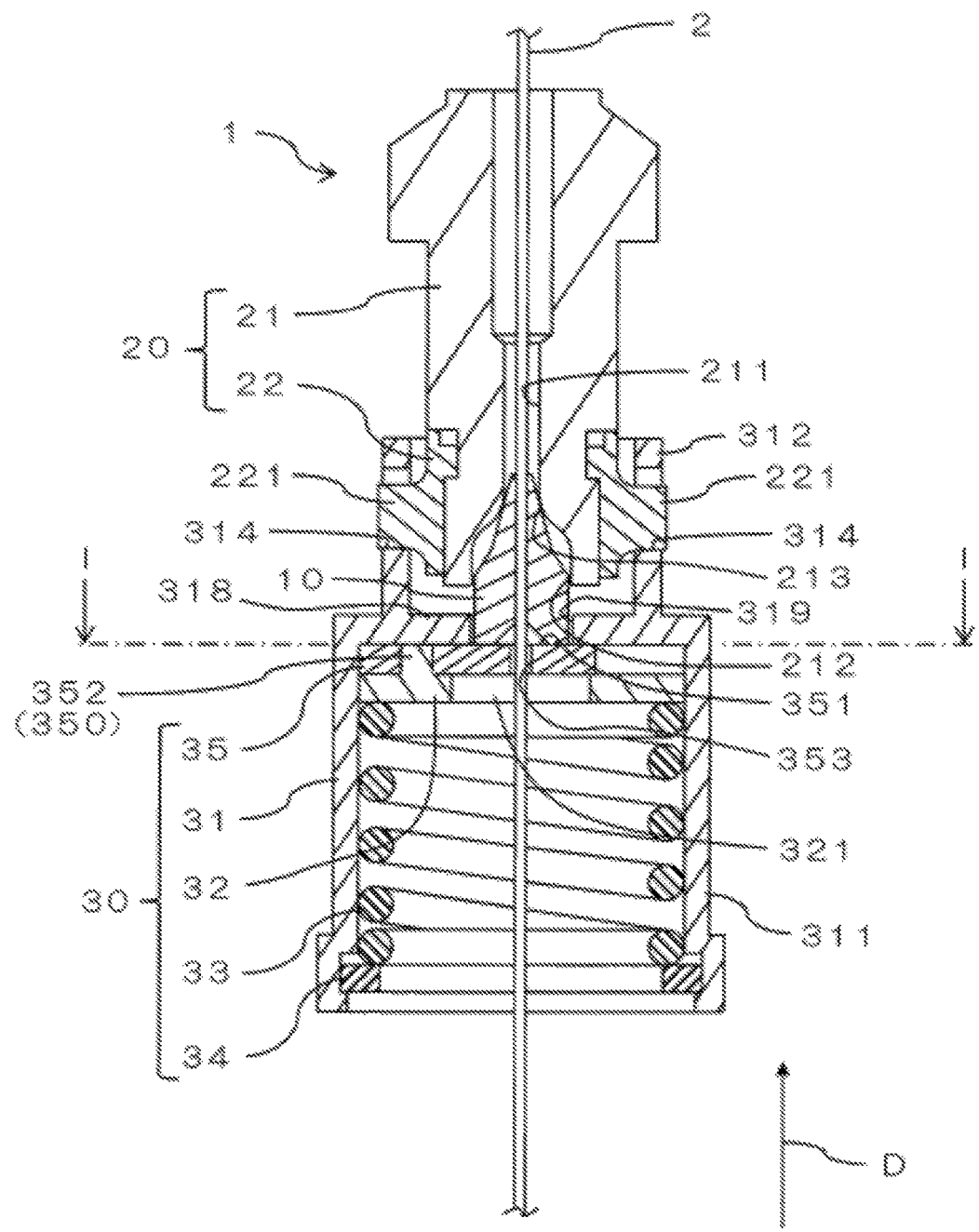
FIG. 4A is a cross-sectional view of the column attachment device shown in FIG. 2 and shows a case in which a pressing plate is in a contacting state.
Figure 4B:
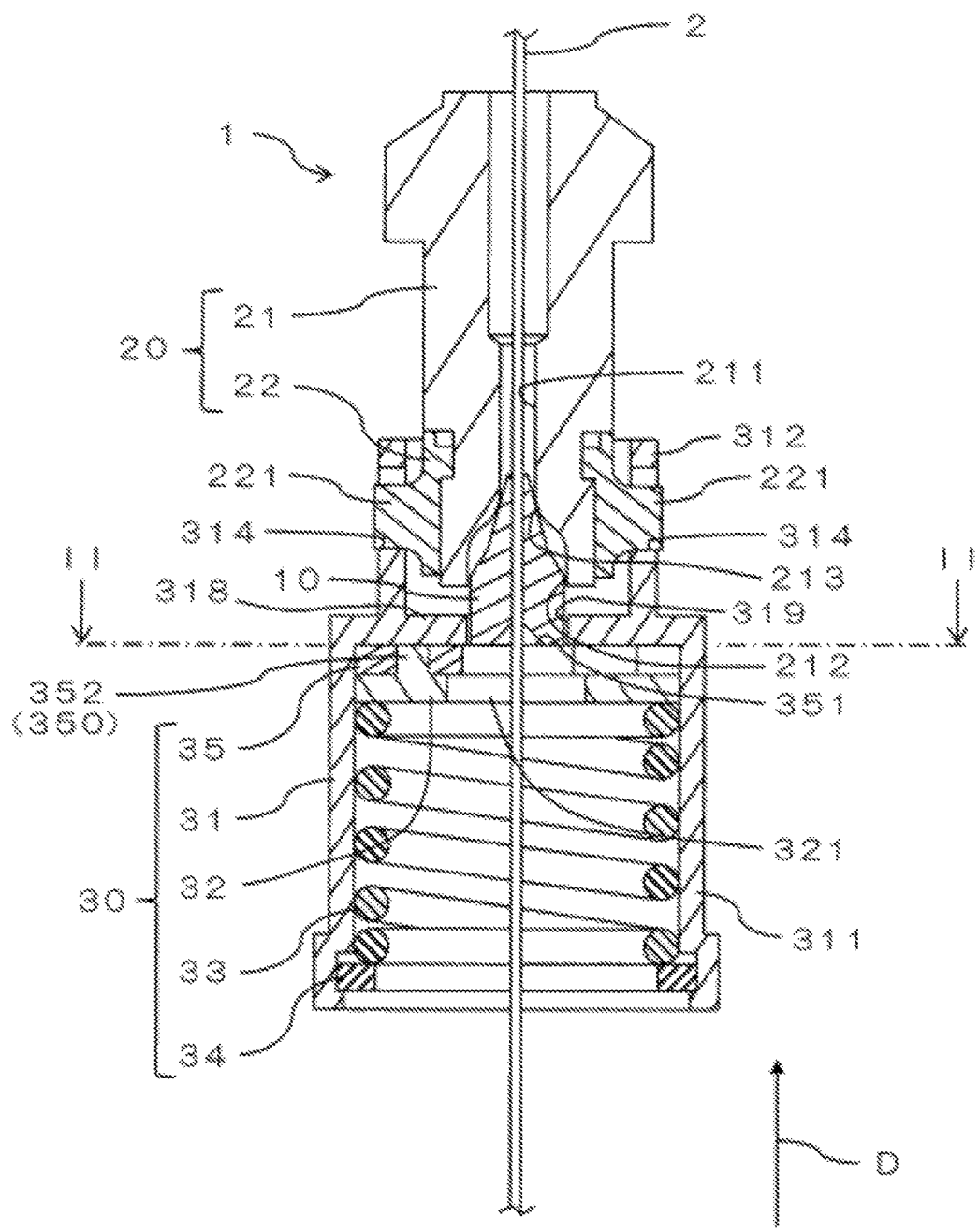
FIG. 4B is a cross-sectional view of the column attachment device shown in FIG. 2 and shows a case in which the pressing plate is in a non-contacting state.
Figure 5A:
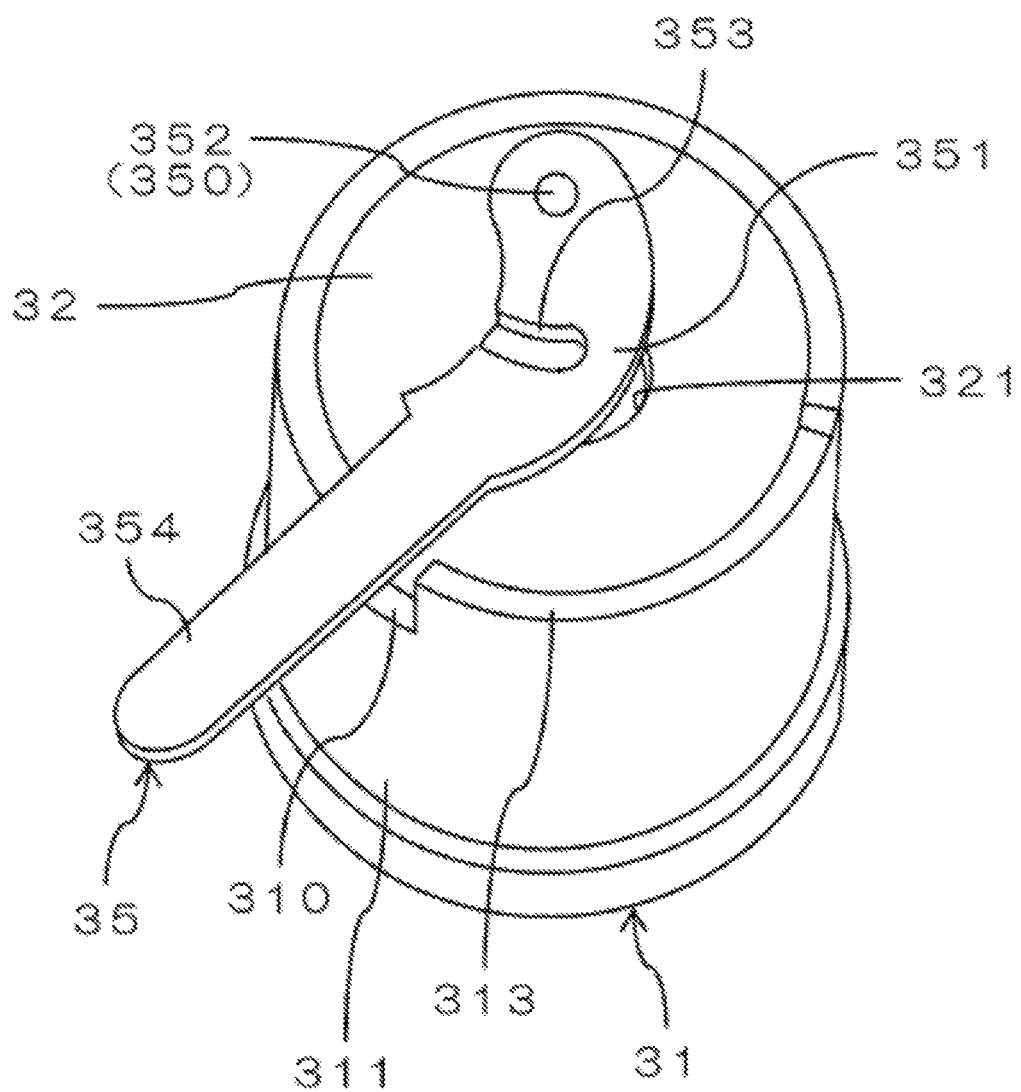
FIG. 5A is a perspective view as seen from a I-I cross-section of FIG. 4A.
Figure 5B:
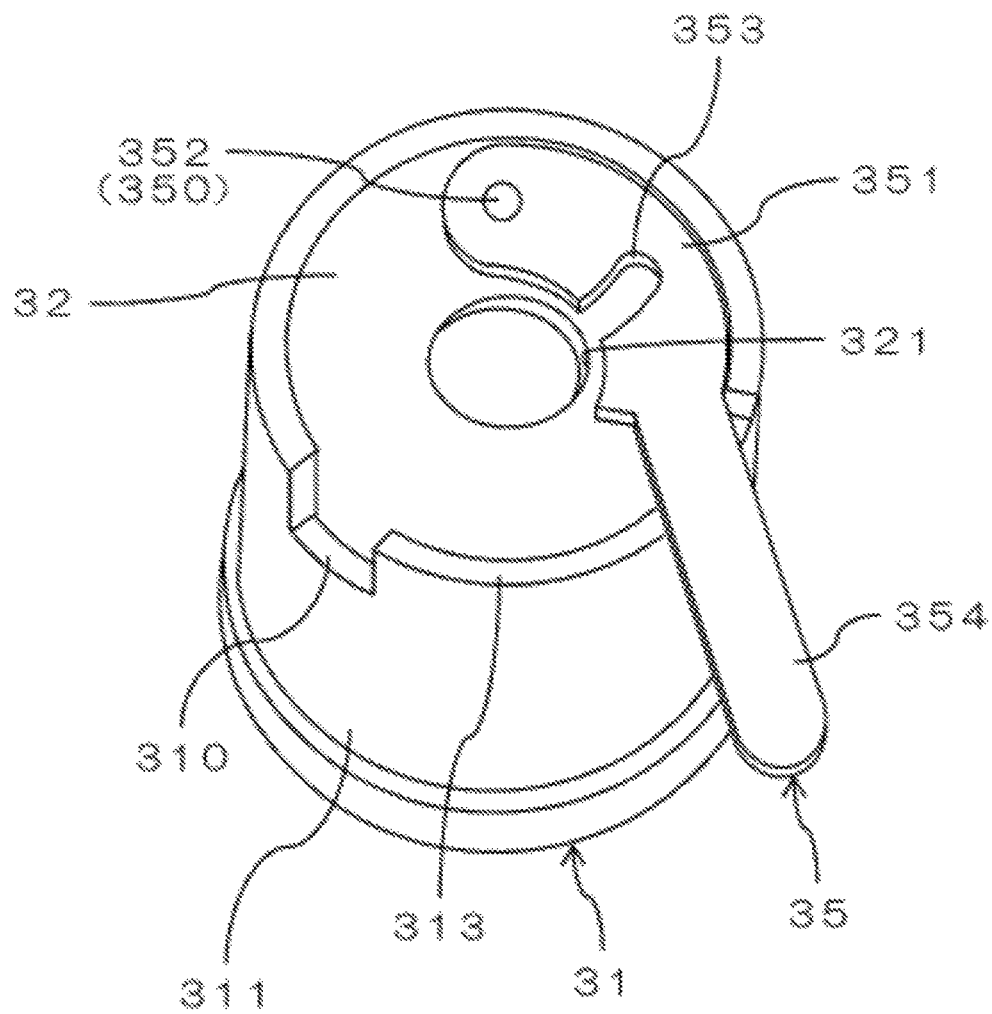
FIG. 5B is a perspective view as seen from a II-II cross-section of FIG. 4B.

FIG. 4A is a cross-sectional view of the column attachment device 1 shown in FIG. 2, and shows a case in which the pressing plate 35 is in the contacting state. FIG. 4B is a cross-sectional view of the column attachment device 1 shown in FIG. 2, and shows a case in which the pressing plate 35 is in the non-contacting state. FIG. 5A is a perspective view of the I-I cross-section of FIG. 4A. FIG. 5B is a perspective view of a II-II cross-section of FIG. 4B.

The ferrule receiving part 20 is equipped with, for example, a receiving side body 21 and a connecting portion 22. The receiving side body 21 is a cylindrical member having a through-hole 211 formed therein. Final tightening is performed in a state in which one end portion of the receiving side body 21 is fixed to the attachment position and the ferrule 10 is pressed against the other end portion of the receiving side body 21.

At the other end surface of the receiving side body 21, an accommodation recess 212 is formed to accommodate the ferrule 10. The accommodation recess 212 has an inner diameter slightly larger than the outer diameter of the other end part side of the ferrule 10, and the ferrule 10 to be inserted to the inside of the accommodation recess 212 from the tapered one end part side thereof is positioned in a state in which the ferrule 10 is accommodated in the accommodation recess 212 up to the other end part side thereof.

The accommodation recess 212 has a narrowed bottom portion, and is communicated with the through-hole 211 via a stepped portion 213. One end part side of the ferrule 10 accommodated in the accommodation recess 212 is brought into close contact with the aforementioned stepped portion 213, so that the airtightness to the ferrule 10 at the stepped portion 213 can be secured. In this embodiment, since the stepped portion 213 is formed into a curved surface, the pressing force applied at the time of final tightening is dispersed, which can prevent an excessive pressing force from being applied to the column 2.

The connecting portion 22 is a cylindrical member fitted on the outer peripheral surface of the other end portion of the receiving side body 21, and is configured to connect the ferrule pressing part 30 to the ferrule receiving part 20. On the outer peripheral surface of the connecting portion 22, a pair of columnar shaped pins 221 protruded in the radial direction of the connecting portion 22 are formed. The pair of pins 221 are arranged symmetrically on both sides sandwiching the center axis line of the connecting portion 22. It should be noted that the connecting portion 22 is not limited to the configuration in which the connecting portion 22 is provided so as to be separated from the receiving side body 21, and the connecting portion 22 may be configured so as to be integrally formed with the receiving side body 21.

The ferrule pressing part 30 is provided with, in addition to the aforementioned pressing plate 35, for example, a pressing side body 31, a spacer 32, an urging member 33, and a fixture 34. The pressing side body 31 is a cylindrical member having an outer diameter larger than the ferrule receiving part 20, and in its inside, the pressing plate 35, the spacer 32, the urging member 33, and the fixture 34 are accommodated.

The pressing side body 31 is a high heat resistance member made of, e.g., a nickel-base superalloy, and has a configuration integrally provided with a first cylindrical portion 311 and a second cylindrical portion 312. In the first cylindrical portion 311, the pressing plate 35, the spacer 32, the urging member 33, and the fixture 34 are accommodated in this order from the second cylindrical portion 312 side.

The second cylindrical portion 312 is small in diameter than the first cylindrical portion 311, and is connected to the ferrule receiving part 20 at the time of final tightening. The second cylindrical portion 312 is provided with a pair of guide grooves 314 for guiding the pair of pins 221 formed on the connecting portion 22 of the ferrule receiving part 20. Each guide groove 314 has approximately the same width as the outer diameter of each pin 221, so that pressing of the ferrule pressing part 30 toward the ferrule receiving part 20 side while guiding each pin 221 along each guide groove 314 results in a mutual connection of the ferrule receiving part 20 and the ferrule pressing part 30.

Now, describing the specific configuration of the guide groove 314 with reference to FIG. 2, the guide groove 314 formed in the second cylindrical portion 312 of the pressing side body 31 includes an introduction groove 315, an inclination groove 316, and an engaging groove 317. The guide groove 314 is configured by a cutout formed at the end face of one end portion of the pressing side body 31, and the introduction groove 315, the inclination groove 316, and the engaging groove 317 are communicated in this order.

The introduction groove 315 extends from the end face of one end portion of the pressing side body 31 in parallel to the axis direction of the pressing side body 31. The inclination groove 316 extends in the direction inclined with respect to the introduction groove 315, i.e., in the direction inclined with respect to the pressing direction D of the ferrule pressing part 30 toward the ferrule receiving part 20 side.

The engaging groove 317 is formed at an end portion of the inclination groove 316 opposite to the introduction groove 315 side, and prevents dropping of the pin 221 from the guide groove 314 by engaging the pin 221 guided along the inclination groove 316. In this example, it is configured such that the engaging groove 317 is formed into a shape dented in the pressing direction D of the ferrule pressing part 30 from the boundary portion to the inclination groove 316 so that the pin 221 is not pulled out of the engaging groove 317 by being engaged with the boundary portion.

At the time of performing the final tightening, when the ferrule pressing part 30 is pressed toward the ferrule receiving part 20 side, the pin 221 is introduced in the guide groove 314 along the introduction groove 315. Thereafter, by pressing the ferrule pressing part 30 while rotating it so that the pin 221 is guided along the inclination groove 316, the ferrule 10 is pressed on the ferrule receiving part 20 side. By pressing the ferrule pressing part 30 until the pin 221 is engaged with the engaging groove 317, the ferrule pressing part 30 is attached to the ferrule receiving part 20, so that the ferrule 10 is pinched between the ferrule receiving part 20 and the ferrule pressing part 30 and fixed thereto.

However, the shape of the guide groove 314 is not limited to the shape shown in FIG. 2, and any arbitral shape may be employed. That is, the shapes of the introduction groove 315, the inclination groove 316 and the engaging groove 317 are not limited to the shapes shown in FIG. 2. The guide groove 314 is not limited to have a configuration equipped with the introduction groove 315, the inclination groove 316, and the engaging groove 317, and may be configured to equip another groove.

Further, the pin 221 and the guide groove 314, which are engaged with each other, are not limited to be configured such that a pair of pins and a pair of guide grooves are provided, but it may be configured such that one pin and one guide groove are provided, or that three or more pins and three of more guide grooves are provided. Further, it may be configured such that the pin 221 is provided at the ferrule pressing part 30 side and the guide groove 314 is provided at the ferrule receiving part 20 side. Further, the pressing side body 31 is not limited to a configuration in which the first cylindrical portion 311 and the second cylindrical portion 312 different in outer diameter are integrally provided. For example, the pressing side body 31 may be configured by one cylindrical portion having a uniform outer diameter, or may be configured such that three or more cylindrical portions different in outer diameter are integrally provided.

Again referring to FIG. 4A, FIG. 4B, FIG. 5A, and FIG. 5B, in the pressing plate 35, a pressing surface 351 for pressing the ferrule 10 is formed. The pressing surface 351 is a flat surface perpendicular to the axis line direction (insertion direction of the column 2) of the ferrule pressing part 30. The pressing plate 35 is rotatably supported centering on the shaft portion 352 fixed to one end portion of the pressing plate. The shaft portion 352 extends along the axis line direction of the ferrule pressing part 30, and the pressing plate 35 is rotatable within a plane perpendicular to the axis line direction. The shaft portion 352 configures a displacing mechanism 350 that switches the pressing plate 35 between a contacting state and a non-contacting state by displacing (rotating) the pressing plate 35.

At a part of the pressing surface 351 of the pressing plate 35, a through-hole 353 for inserting the column 2 is formed. The through-hole 353 is configured by a cutoff formed in the peripheral portion of the pressing plate 35. The through-hole 353 is formed into, for example, an arc shape centering on the shaft portion, so that the column 2 can be smoothly taken in and out along the arc-shaped through-hole 353 when the pressing plate 35 is rotated centering on the shaft portion 352.

A part of the pressing plate 35 extends to the outside of the pressing side body 31, the portion protruded from the pressing side body 31 configures an operation portion 354 operated by an operator when rotating the pressing plate 35. In the first cylindrical portion 311 of the pressing side body 31, a guide hole 313 for inserting the operation portion 354 and guiding the operation portion 354 in a direction perpendicular to the axis line direction of the ferrule pressing part 30 is formed.

The spacer 32 is in contact with a surface of the pressing plate 35 opposite to the pressing surface 351. The shaft portion 352 of the pressing plate 35 is provided to the spacer 32. At the center portion of the spacer 32, a through-hole 321 is formed. A column 2 is inserted in the through-hole 321. The through-hole 321 has an inner diameter larger than the outer diameter of the ferrule 10, and is formed into a shape through which the ferrule 10 can pass.

When the pressing plate 35 is in a contacting state with respect to the ferrule 10, as shown in FIG. 4A and FIG. 5A, it is in a state in which the pressing plate 35 faces the ferrule 10 and the through-hole 321 of the spacer 32 is covered by the pressing plate 35. On the other hand, when the pressing plate 35 is in a non-contacting state with respect to the ferrule 10, as shown in FIG. 4B and FIG. 5B, it is in a state in which the pressing plate 35 is retracted to the position where the pressing plate 35 does not face the ferrule 10 and the through-hole 321 of the spacer 32 is opened so that the ferrule 10 can pass through the inside of the ferrule pressing part 30 via the through-hole 321.

As described above, in this embodiment, by displacing the pressing plate 35 to switch the pressing plate 35 to the non-contacting state, it becomes possible for the ferrule 10 to pass through the inside of the ferrule pressing part 30, and therefore the ferrule pressing part 30 can be extracted from the ferrule 10 side. Therefore, the ferrule pressing part 30 can be removed from the column 2 in a state in which the ferrule 10 is swagedly attached to the column 2. Further, by displacing the pressing plate 35 to switch the pressing plate 35 to the contacting state, the ferrule 10 is pressed by the pressing plate 35 toward the ferrule receiving part 20 side, and therefore the ferrule 10 can be assuredly fixed between the ferrule receiving part 20 and the ferrule pressing part 30.

Further, in this embodiment, with a simple configuration of simply rotating the pressing plate 35 centering on the shaft portion 352, the pressing plate 35 can be switched between the contacting state and the non-contacting state. Especially, since the operation portion 354 to be operated by an operator is provided at the pressing plate 35 and the operation portion 354 is protruded from the ferrule pressing part 30, with a more simple configuration of simply operating the operation portion 354, the pressing plate 35 can be switched between the contacting state and the non-contacting state.

The urging member 33 is configured by, for example, a compression spring, and arranged so as to extend in the axis line direction of the ferrule receiving part 20 and the ferrule pressing part 30. One end face of the urging member 33 is in contact with the rear surface (surface opposite to the pressing plate 35 side) of the spacer 32. On the other hand, the other surface of the urging member 33 is in contact with the fixture 34 at the end portion of the second cylindrical portion 312. The fixture 34 is configured by, for example, a C-shaped retaining ring, and is fixed to the end portion of the second cylindrical portion 312 in a state in which an urging force of a certain degree is urged in the urging member 33. However, the urging member 33 is not limited to a compression spring, and may be configured by other elastic members, such as, e.g., a rubber, or may be configured by a member other than an elastic member.

When performing the final tightening, in a state in which a ferrule 10 is arranged on the pressing surface 351 of the pressing plate 35 set to the contacting state, the ferrule pressing part 30 is approached to the ferrule receiving part 20 to position the ferrule 10 in the accommodation recess 212. From this state, the ferrule pressing part 30 is pressed toward the ferrule receiving part 20 side against the urging force of the urging member 33 and the pins 221 and the guide grooves 314 are engaged. As a result, the ferrule 10 is pressed from the other end part side toward the ferrule receiving part 20 side. In a state in which the ferrule pressing part 30 is attached to the ferrule receiving part 20, the ferrule 10 is sandwiched between the ferrule receiving part 20 and the ferrule pressing part 30 and fixed thereto.

As described above, in this embodiment, when the pressing plate 35 is in a contact state, the ferrule 10 is urged toward the ferrule receiving part 20 side with the pressing plate 35. Therefore, the ferrule 10 can be pressed toward the ferrule receiving part 20 side by a sufficient pressing force with the urging force of the urging member 33. Especially, since the urging force of the urging member 33 acts on the ferrule 10 via the pressing plate 35, rattling of the pressing plate 35 can be prevented. Further, by the urging force of the urging member 33, the pressing plate 35 can be stably held in a contacting state or a non-contacting state.

When the ferrule pressing part 30 is attached to the ferrule receiving part 20, the ferrule pressing part 30 is pushed toward the ferrule receiving part 20 side against the urging force of the urging member 33, causing a shrinkage of the urging member 33. As a result, the pressing plate 35 is also pressed downward. In this embodiment, a retracting portion 310 dented in a direction opposite to the pressing direction D of the ferrule pressing part 30 is formed in a part of the guide hole 313, so that the operation portion 354 can be retracted in the retracting portion 310.

Specifically, when the pressing plate 35 is in a contacting state with respect to the ferrule 10, as shown in FIG. 5A, the operation portion 354 faces the retracting portion 310. In this state, when the ferrule pressing part 30 is pushed toward the ferrule receiving part 20 side, the operation portion 354 is entered in the retracting portion 310. Therefore, the operation portion 354 can be pushed downward without coming into contact with the pressing side body 31.

In the pressing side body 31, an inner wall 318 protruding from, e.g., the inner surface of the boundary portion of the first cylindrical portion 311 and the second cylindrical portion 312 is formed. The pressing plate 35 is in a press-contact with the inner wall 318 by the urging force of the urging member 33. The inner wall 318 protrudes toward the central axis line side along the radial direction of the pressing side body 31, and a through-hole 319 is formed at the center portion of the inner wall 318. The through-hole 321 has an inner diameter slightly larger than the outer diameter of the other end part side (pressing plate 35 side) of the ferrule 10.

At the time of the final tightening, the other end portion of the ferrule 10 is positioned in a state of being accommodated in the through-hole 319. As described above, the ferrule 10 is positioned by the accommodation recess 212 of the ferrule receiving part 20 side and the through-hole 319 of the ferrule pressing part 30 side, so that the one end part side of the ferrule 10 can be assuredly adhered to the stepped portion 213. Further, at the time of switching the pressing plate 35 between the contacting state and the non-contacting state, the displacement of the ferrule 10 accommodated in the through-hole 319 can be prevented. As a result, thereafter, the ferrule pressing part 30 can be smoothly extracted from the ferrule 10 side.

Figure 6A:
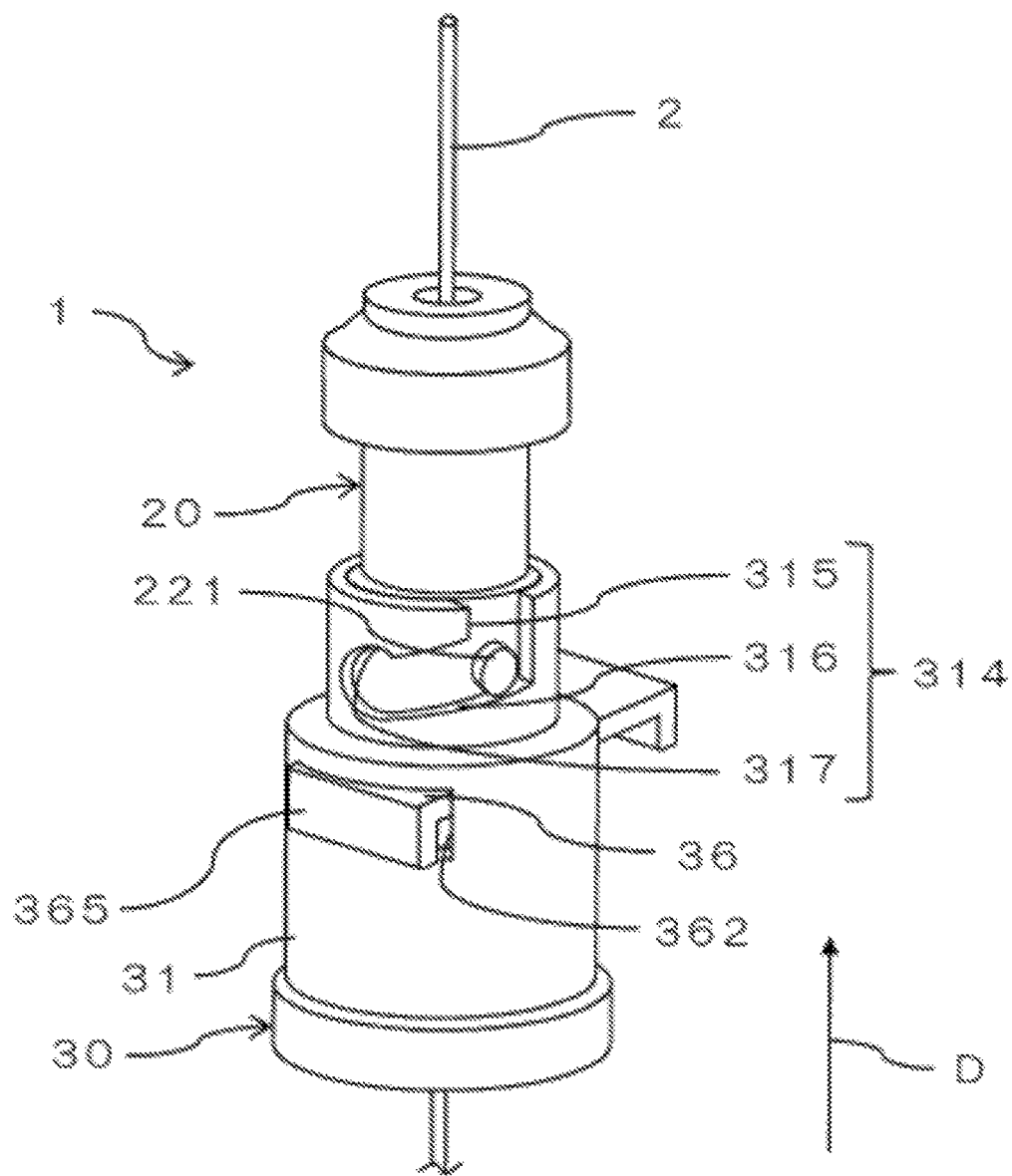
FIG. 6A is a perspective view showing a configuration example of a column attachment device according to a second embodiment of the present invention.
Figure 6B:
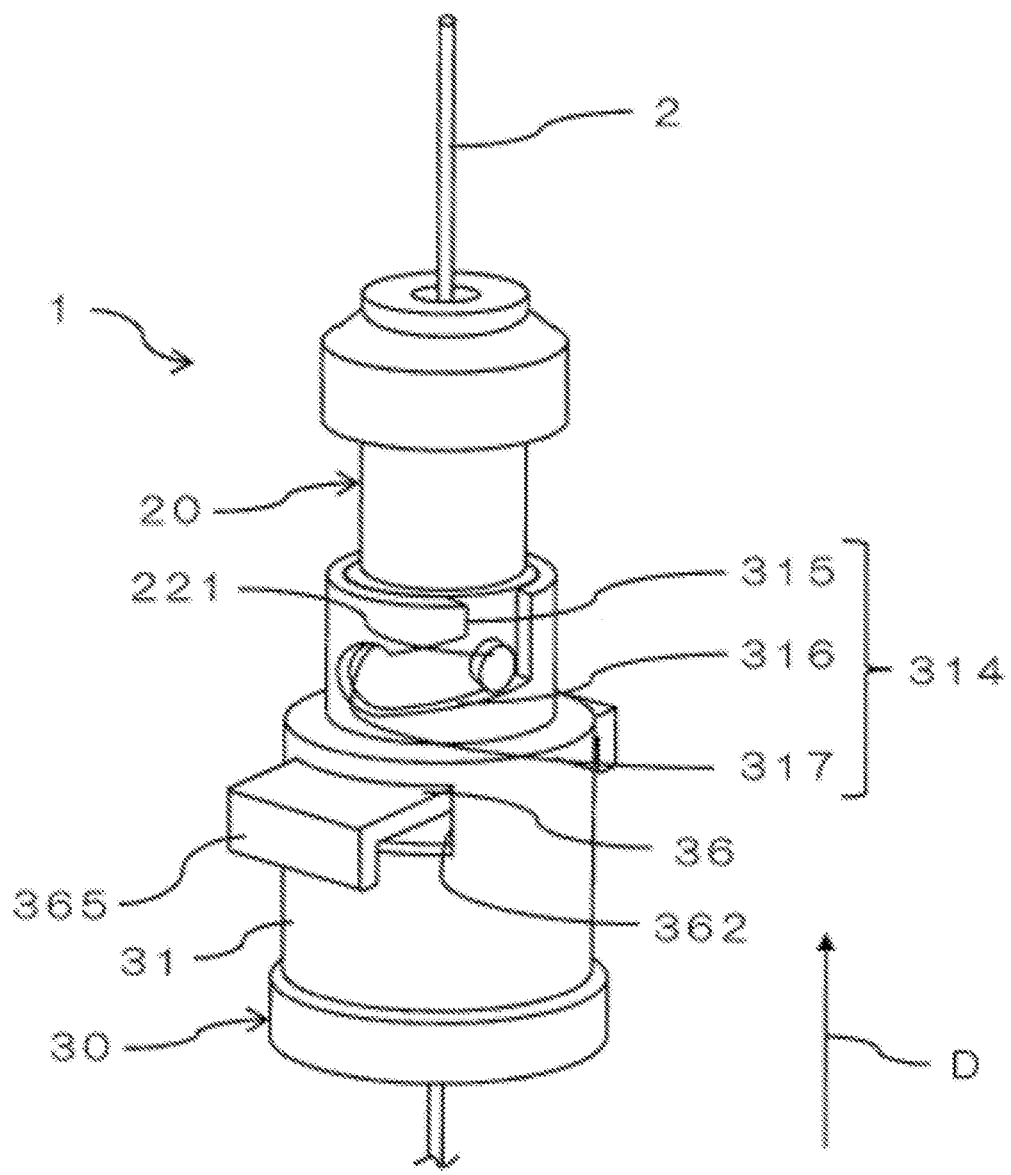
FIG. 6B is a perspective view showing a configuration example of the column attachment device according to the second embodiment of the present invention.
Figure 7A:
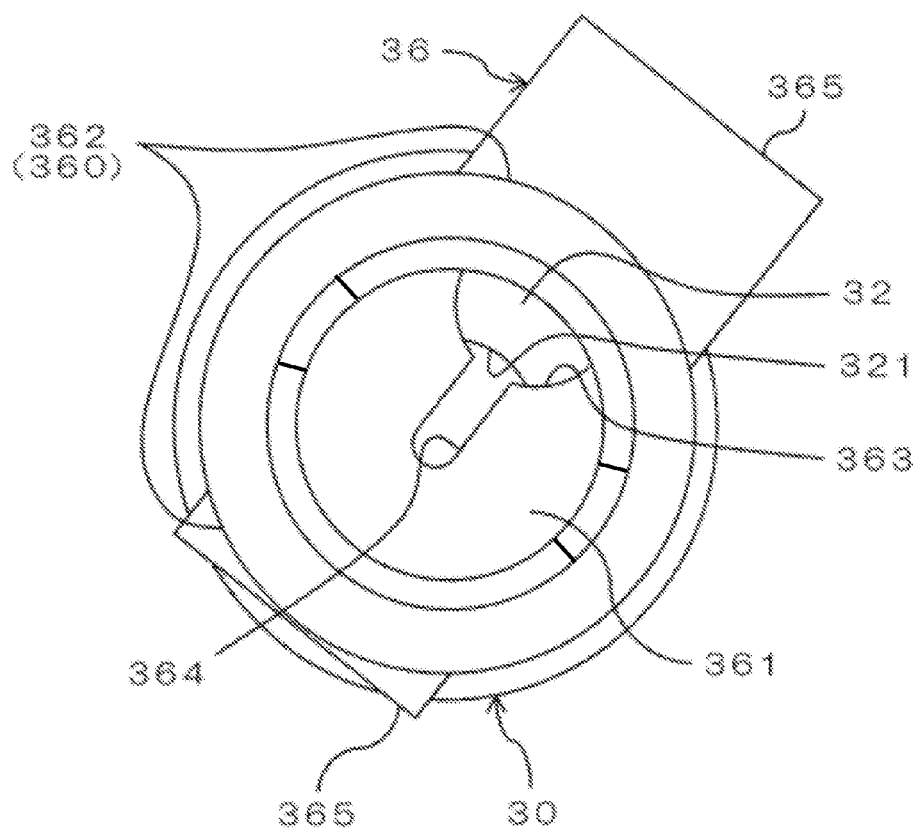
FIG. 7A is a plan view of a ferrule pressing part of the column attachment device shown in FIG. 6A and shows a case in which a pressing plate is in a contacting state.
Figure 7B:
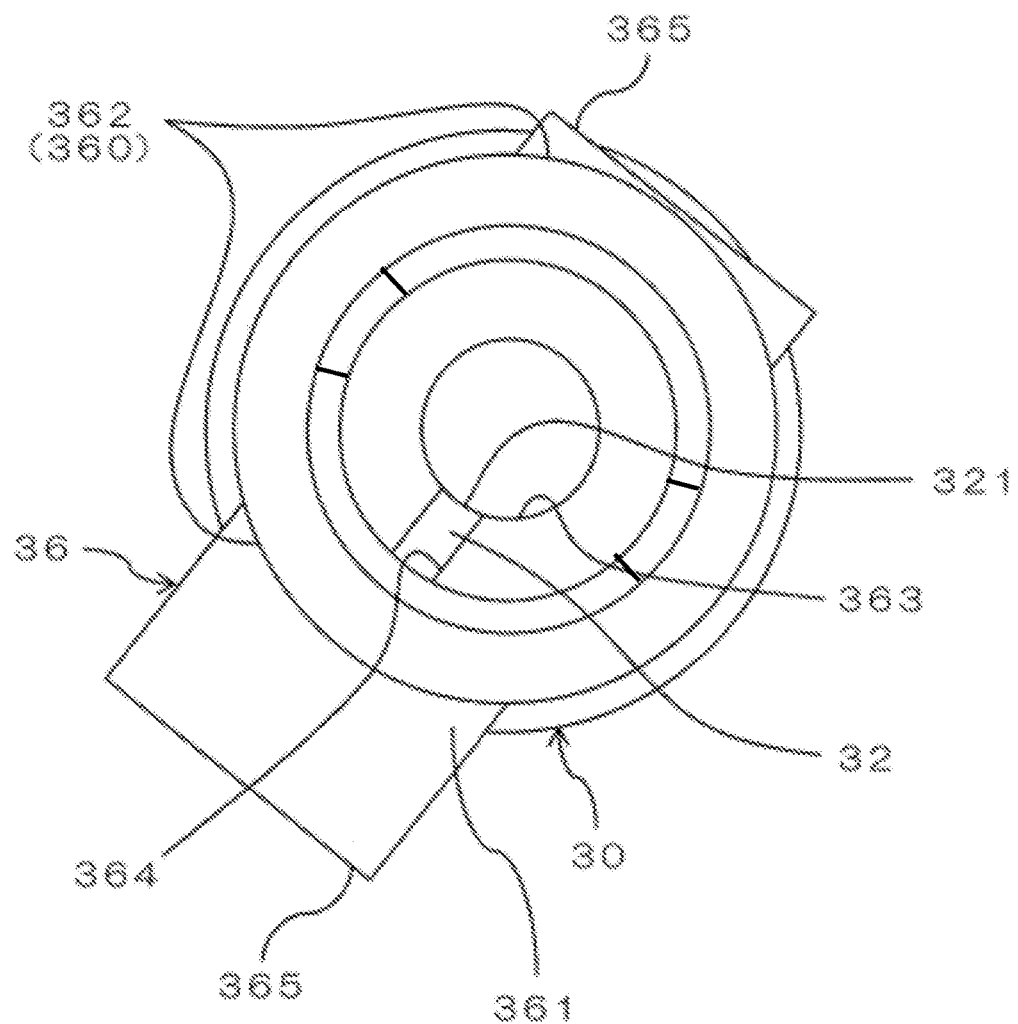
FIG. 7B is a plan view of a ferrule pressing part of the column attachment device shown in FIG. 6B and shows a case in which a pressing plate is in a non-contacting state.

FIG. 6A and FIG. 6B are perspective views each showing a configuration example of the column attachment device 1 according to a second embodiment of the present invention. FIG. 7A is a plan view of a ferrule pressing part 30 of the column attachment device 1 shown in FIG. 6A and shows a case in which a pressing plate 36 is in a contacting state. FIG. 7B is a plan view of the ferrule pressing part 30 of the column attachment device 1 shown in FIG. 6B and shows a case in which the pressing plate 36 is in a non-contacting state.

In the aforementioned first embodiment, the description was directed to a configuration in which the pressing plate 35 is rotatable centering on the shaft portion 352. On the other hand, in the second embodiment, the pressing plate 36 is configured to be slidable. In the pressing side body 31 of the ferrule pressing part 30, in addition to the aforementioned pressing plate 36, in the same manner as in the first embodiment, a spacer 32, an urging member 33, and a fixture 34 are provided. In the second embodiment, as to the same configuration as in the first embodiment, the detail description will be omitted by allotting the same symbol in the figure.

In the pressing plate 36, a pressing surface 361 for pressing the ferrule 10 is formed. The pressing surface 361 is a flat surface perpendicular to the axis line direction (insertion direction of the column 2) of the ferrule pressing part 30. In the pressing side body 31, a guide portion 362 configured by a pair of through-holes formed in the peripheral surface of the pressing side body 31, so that the pressing plate 36 is slidably held by the guide portion 362.

The pair of through-holes configuring the guide portion 362 are symmetrically arranged on both sides of the central axis line of the pressing side body 31. Each through-hole is formed to have approximately the same width as the width of the pressing plate 36, and the pressing plate 36 is inserted into the through-holes, so that the pressing plate 36 is slidably in one direction in a plane perpendicular to the axis line direction of the ferrule pressing part 30. The guide portion 362 configures a displacing mechanism 360 that switches the pressing plate 36 between a contacting state and a non-contacting state by displacing (sliding) the pressing plate 36.

Further, in the pair of through-holes configuring the guide portion 362, the length of the pressing direction D is formed to be larger than the thickness of the pressing plate 36. With this, in the same manner as in the first embodiment, when the ferrule pressing part 30 is pressed toward the ferrule receiving part 20 side, the pressing plate 36 can be retracted in each through-hole, so that the pressing plate 36 can be pushed downward without coming into contact with the pressing side body 31.

At a part of the pressing surface 361 of the pressing plate 36, a first through-hole 363 for allowing the insertion of the ferrule 10 and a second through-hole 364 for allowing the insertion of column 2 are formed. The through-hole 363 has an inner diameter larger than the outer diameter of the ferrule 10, and is formed into a shape through which the ferrule 10 can pass. The second through-hole 364 is configured by a cutoff formed in the inner peripheral portion of the first through-hole 363. The second through-hole 364 is formed into, for example, a linear shape along the sliding direction of the pressing plate 36, so that the column 2 can be smoothly taken in and out along the second through-hole 364 when the pressing plate 36 is slidably moved.

Both end portions of the pressing plate 36 in the sliding direction are protruded outside the pressing side body 31. Both the end portions are each formed into a shape bent in a direction perpendicular to the sliding direction, and configure operation portions 365 to be operated by an operator when sliding the pressing plate 36. The operation portion 365 also functions as stoppers for preventing the pressing plate 36 from being dropped from the guide portion 362. However, the shape of the operation portion 365 is not limited to the same described above.

When the pressing plate 36 is in a contacting state with respect to the ferrule 10, as shown in FIG. 7A, the first through-hole 363 of the pressing plate 36 does not face the through-hole 321 of the spacer 32 and only the second through-hole 364 faces the through-hole 321 of the spacer 32, so that it is in a state in which the through-hole 321 of the spacer 32 is closed by the pressing plate 36. On the other hand, when the pressing plate 36 is in a non-contacting state with respect to the ferrule 10, as shown in FIG. 7B, the first through-hole 363 of the pressing plate 36 faces the through-hole 321 of the spacer 32 and therefore the through-hole 321 of the spacer 32 is opened, so that it is in a state in which the ferrule 10 can pass through the inside of the ferrule pressing part 30 via the through-hole 321.

As described above, in this embodiment, by displacing the pressing plate 36 to switch the pressing plate 36 to the non-contacting state, it becomes possible for the ferrule 10 to pass through the inside of the ferrule pressing part 30, and therefore the ferrule pressing part 30 can be extracted from the ferrule 10 side. Therefore, the ferrule pressing part 30 can be removed from the column 2 in a state in which the ferrule 10 is swagedly attached to the column 2. Further, by displacing the pressing plate 36 to change the pressing plate 36 to the contacting state, the ferrule 10 is pressed by the pressing plate 36 toward the ferrule receiving part 20 side, and therefore the ferrule 10 can be assuredly fixed between the ferrule receiving part 20 and the ferrule pressing part 30.

Further, in this embodiment, with a simple configuration of simply slidably moving the pressing plate 36, the pressing plate 36 can be switched between the contacting state and the non-contacting state. Especially, since the operation portion 365 to be operated by an operator is provided at the pressing plate 36 and the operation portion 365 is protruded from the ferrule pressing part 30, with a more simple configuration of simply operating the operation portion 365, the pressing plate 36 can be switched between the contacting state and the non-contacting state.

In this embodiment, although the guide portion 362 is configured by a pair of through-holes, but not limited to it, and any arbitral configurations may be employed as long as the guide portion 362 can be configured to slidably hold the pressing plate 36. Further, in this embodiment, although the spacer 32 is provided, the spacer 32 may be omitted.

Figure 8:
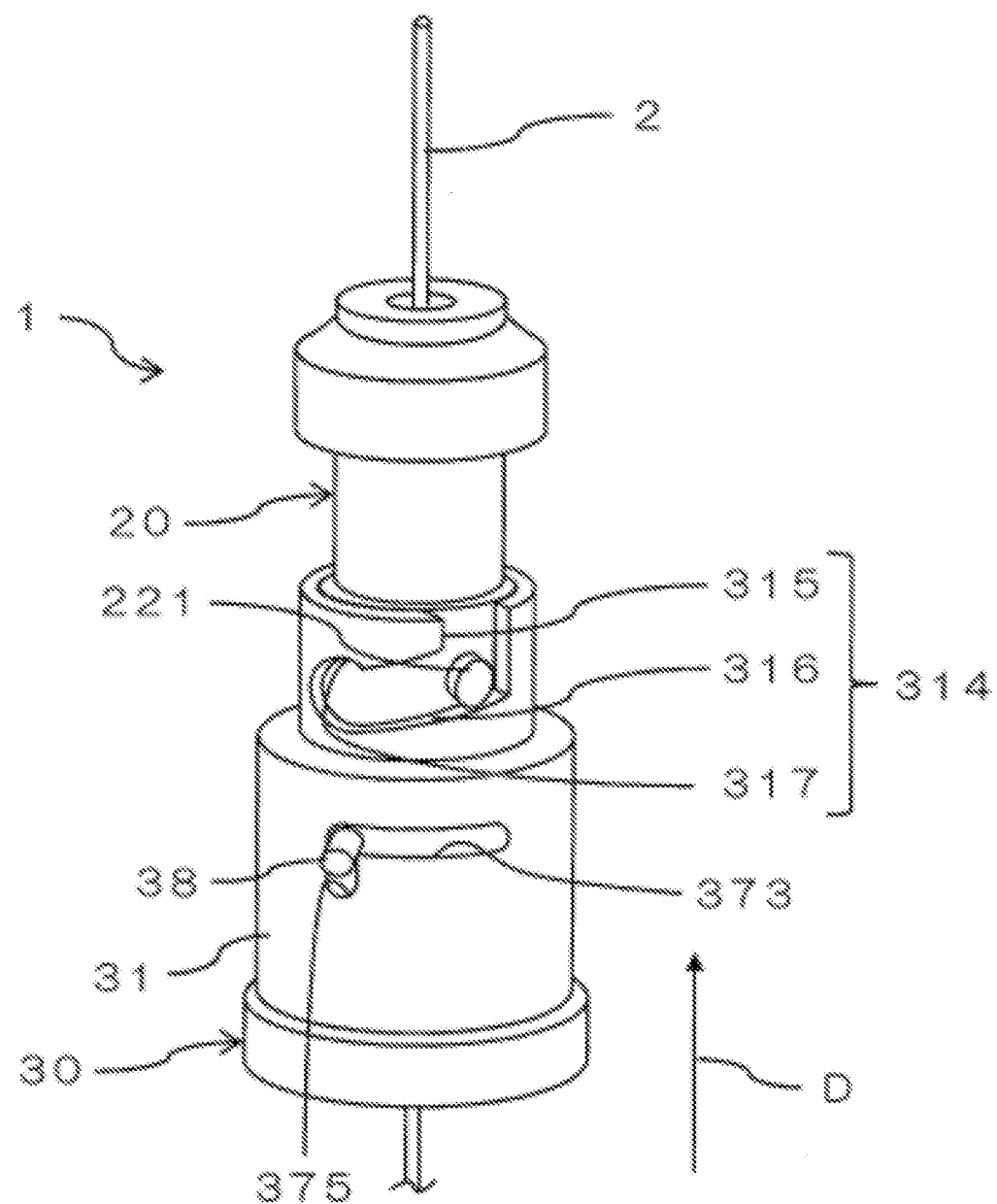
FIG. 8 is a perspective view showing a configuration example of a column attachment device according to a third embodiment of the present invention.
Figure 9:
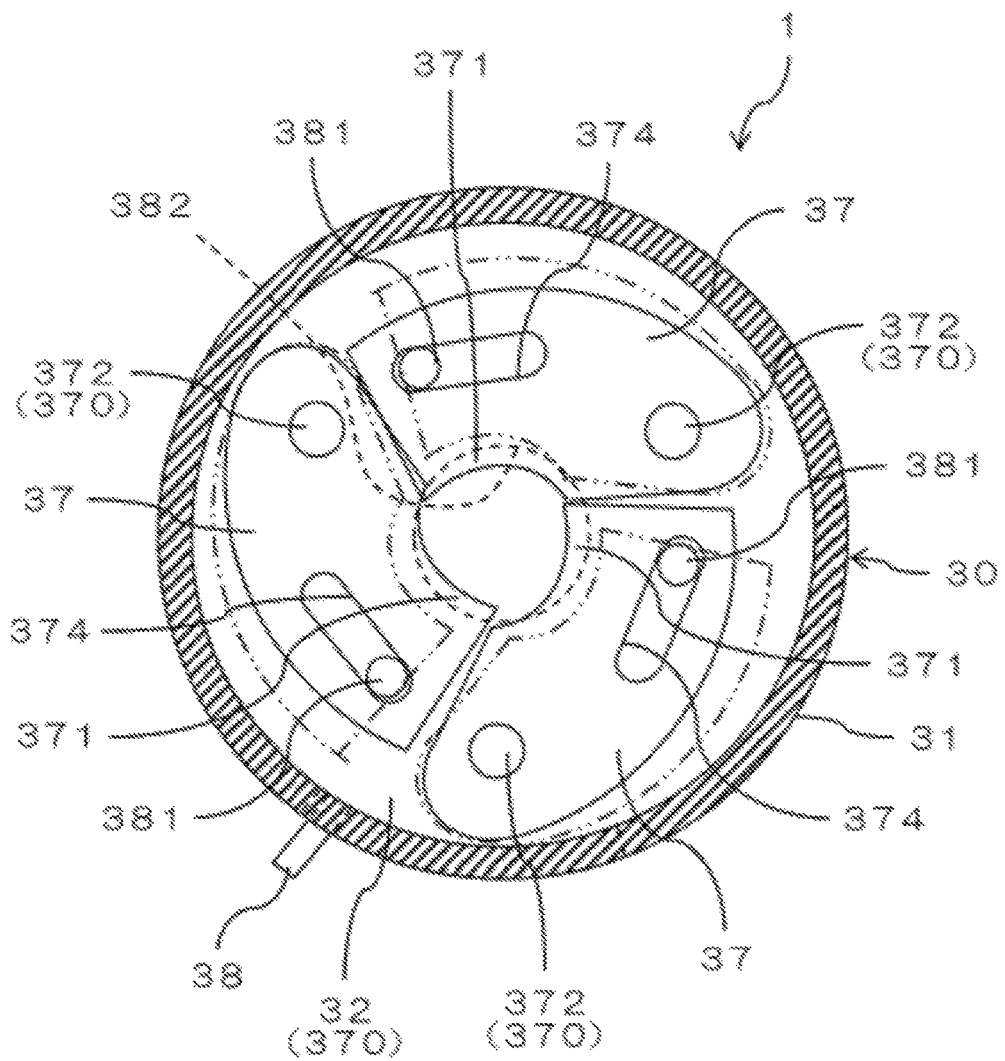
FIG. 9 is a cross-sectional view of the column attachment device shown in FIG. 8 and shows a case in which a pressing plate is in a contacting state.
Figure 10A:
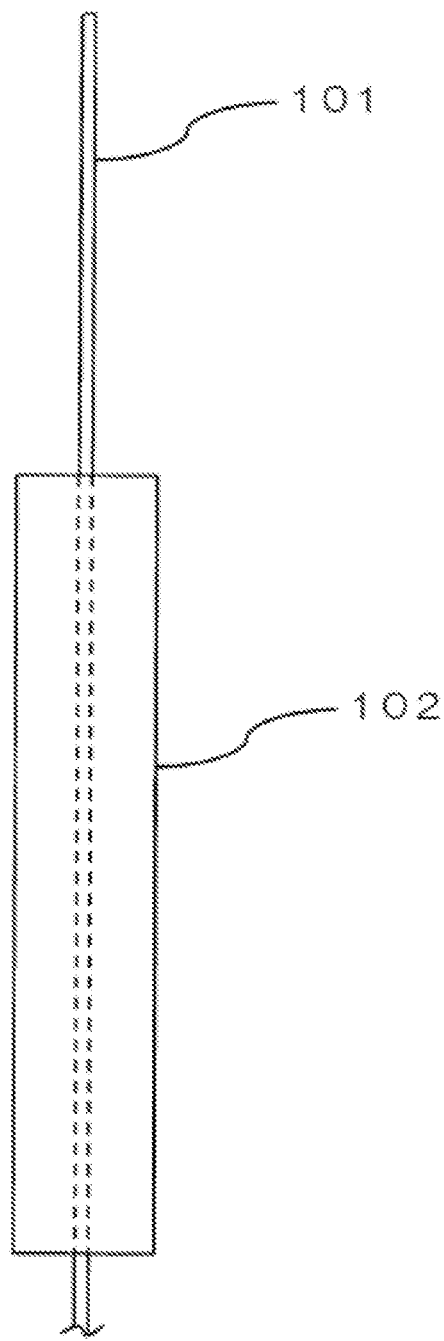
FIG. 10A is a schematic cross-sectional view for explaining an attachment work flow of the column.
Figure 10B:
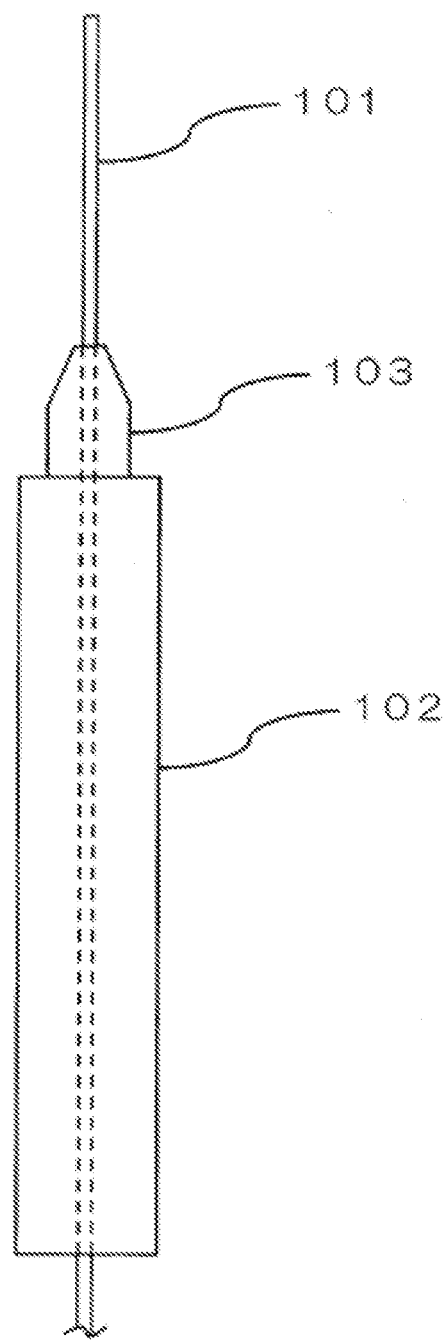
FIG. 10B is a schematic cross-sectional view for explaining the attachment work flow of the column.
Figure 10C:
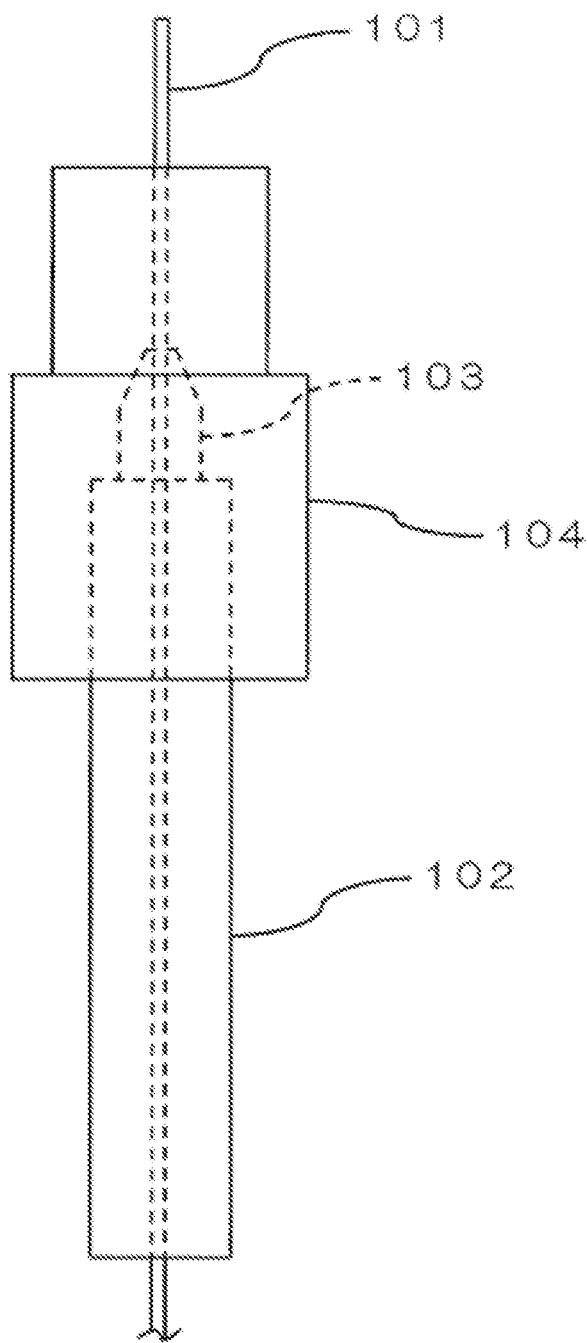
FIG. 10C is a schematic cross-sectional view for explaining the attachment work flow of the column.

FIG. 8 is a perspective view showing a configuration example of a column attachment device 1 according to a third embodiment of the present invention. FIG. 9 is a cross-sectional view of the column attachment device 1 shown in FIG. 8, and shows a case in which a pressing plate 37 is in a contacting state. In the aforementioned first embodiment, the description was directed to a configuration in which one pressing plate 35 is rotatable centering on the shaft portion 352. On the other hand, in the third embodiment, it is configured such that a plurality of pressing plates 37 are rotatable centering on respective different shaft portions 372.

In the pressing side body 31 of the ferrule pressing part 30, in addition to the aforementioned pressing plate 37, in the same manner as in the first embodiment, a spacer 32, an urging member 33, and a fixture 34 are provided. In the second embodiment, as to the same configuration as in the first embodiment, the detail description will be omitted by allotting the same symbol in the figure.

The plurality of pressing plates 37 have, for example, the same shape, and are provided within the same plane perpendicular to the axis line direction (insertion direction of the column 2) of the ferrule pressing part 30. Each pressing plate 37 is rotatably supported centering on the shaft portion 372 fixed to one end portion of the pressing plate 37. Each shaft portion 372 extends along the axis line direction of the ferrule pressing part 30, and each pressing plate 37 is rotatable within a plane perpendicular to the axis line direction.

In this embodiment, three pressing plates 37 are provided, and the shaft portions 372 each attached to one end portion of each pressing plate 37 are arranged at equal intervals in the circumference direction centering on the center axis line of the ferrule pressing part 30. Further, the other end portion of each pressing plate 37 is arranged close to one end portion of the adjacent pressing plate 37. With this, the pressing plates 37 are arranged in the circumference direction, so that a part of each pressing plate 37 forms a pressing surface 371 for pressing the ferrule 10. Each pressing surface 371 is a flat surface provided in the same plane perpendicular to the axis line direction of the ferrule pressing part 30.

The spacer 32 is configured by, for example, a circular plate provided coaxially with the center axis line of the ferrule pressing part 30, and constitutes a rotary plate by being rotatably attached centering on the center axis line. The spacer 32 is accommodated in the pressing side body 31 (in the first cylindrical portion 311), and a bar-shaped operation portion 38 is protruded radially outward from a part of the outer peripheral surface of the spacer 32. In the pressing side body 31, a guide hole 373 for allowing an insertion of the operation portion 38 and guiding the operation portion 38 in a direction perpendicular to the axis line direction of the ferrule pressing part 30 is formed. With this, an operator can operate the operation portion 38 from the outside of the ferrule pressing part 30 to rotate the spacer 32.

The spacer 32 is in contact with a surface of the pressing surface 371 opposite to the pressing surface 371. The spacer 32 is provided with a shaft portion 372 that rotatably supports each pressing plate 37. Further, the spacer 32 is provided with a guide pin 381 protruded toward the pressing plate 37 side along the axis line direction of the ferrule pressing part 30 corresponding to each pressing plate 37. The guide pins 381 are arranged, in the same manner as the shaft portion 372, at equal intervals in the circumference direction centering on the center axis line of the ferrule pressing part 30.

At the other end portion (a side opposite to the shaft portion 372 side) of each pressing plate 37, a guide groove 374 for guiding the corresponding guide pin 381 is formed. Each guide groove 374 is formed into, for example, a straight shape, and extends obliquely so that the distance to the center axis line of the ferrule pressing part 30 changes. Each guide pin 381 is inserted in the guide groove 374 of the corresponding pressing plate 37, and is slidable from one end of the guide groove 374 to the other end thereof.

With this, when the operation portion 38 is operated and therefore the spacer 32 is rotated centering on the center axis line, each guide pin 381 slides along the corresponding guide groove 374, so that the pressing plates 37 rotate simultaneously centering on the shaft portion 372. Each shaft portion 372 and the spacer (rotary plate) 32 constitutes a displacing mechanism 370 that switches the pressing plate 37 between the contacting state and the non-contacting state by displacing (rotating) each pressing plate 37.

At the center portion of the spacer 32, a through-hole 382 is formed. A column 2 is inserted in the through-hole 382. The through-hole 382 has an inner diameter larger than the outer diameter of the ferrule 10, and is formed into a shape through which the ferrule 10 can pass.

When the pressing plates 37 are in a contacting state with respect to the ferrule 10, as shown in FIG. 9 by a solid line, it is in a state in which a part of each pressing plate 37 faces the through-hole 382 of the spacer 32, so that the through-hole 382 is covered by the pressing plates 37. On the other hand, when the pressing plates 37 are in a non-contacting state with respect to the ferrule 10, as shown in FIG. 9 by a two-dot chain line, the pressing plate 37 is retracted from the through-hole 382 of the spacer 32 and therefore the through-hole 382 is opened, so that it is in a state in which the ferrule 10 can pass through the inside of the ferrule pressing part 30 via the through-hole 382.

As described above, in this embodiment, by displacing the pressing plate 37 to switch the pressing plate 37 to the non-contacting state, it becomes possible for the ferrule 10 to pass through the inside of the ferrule pressing part 30, and therefore the ferrule pressing part 30 can be extracted from the ferrule 10 side. Therefore, the ferrule pressing part 30 can be removed from the column 2 in a state in which the ferrule 10 is swagedly attached to the column 2. Further, by displacing the pressing plate 37 to change the pressing plate 37 to the contacting state, the ferrule 10 is pressed by the pressing plate 37 toward the ferrule receiving part 20 side, and therefore the ferrule 10 can be assuredly fixed between the ferrule receiving part 20 and the ferrule pressing part 30.

Further, in this embodiment, by rotating the spacer (rotary plate) 32 to thereby simultaneously rotate the plurality of pressing plates 37, the pressing plates 37 can be switched between the contacting state and the non-contacting state. Especially, the spacer 32 is configured by, for example, a circular plate provided coaxially with the center axis line of the ferrule pressing part 30, and the spacer 32 rotates centering on the center axis line, and therefore, the plurality of pressing plates 37 simultaneously rotate. As a result, with a simple configuration of simply rotating the circular plate, the pressing plate 37 can be switched between the contacting state and the non-contacting state.

When the ferrule pressing part 30 is attached to the ferrule receiving part 20, the ferrule pressing part 30 is pushed toward the ferrule receiving part 20 side against the urging force of the urging member 33, causing a shrinkage of the urging member 33. As a result, the spacer 32 is also pressed downward. In this embodiment, a retracting portion 375 dented in a direction opposite to the pressing direction D of the ferrule pressing part 30 is formed in a part of the guide hole 373, so that the operation portion 38 can be retracted in the retracting portion 375.

Specifically, when the pressing plate 35 is in a contacting state with respect to the ferrule 10, as shown in FIG. 8, the operation portion 38 faces the retracting portion 375. In this state, when the ferrule pressing part 30 is pushed toward the ferrule receiving part 20 side, the operation portion 38 is entered in the retracting portion 375. Therefore, the operation portion 38 can be pushed downward without coming into contact with the pressing side body 31.

In this embodiment, although it is configured such that three pressing plates 37 are provided, it is not limited to it. It may be configured such that two or four or more pressing plates 37 are provided. Further, the spacer 32 is not limited to a member composed of a circular plate, and any arbitral configuration may be employed as long as it is configured so that the spacer 32 can rotate the pressing plate 37. Further, in this embodiment, although the rotary plate is configured by the spacer 32, the rotary plate can be provided separately from the spacer 32.

In the aforementioned embodiments, the description was directed to the configuration in which the displacing mechanism 350, 360, and 370 rotates or slides the pressing plate 35, 36, and 37. However, the displacing mechanism is not limited to the configuration of rotating or sliding the pressing plate, and may be configured such that the pressing plate is displaced in other manners to switch the pressing plate between the contacting state and the non-contacting state.

Further, in the aforementioned embodiments, the description was directed to the configuration in which the ferrule pressing part 30 is attached to the ferrule receiving part 20 by the engagement of the pin 221 and the guide groove 314. However, it is not limited to such a configuration. The present invention can be applied to various column attachment devices 1, such as, e.g., a column attachment device 1 in which the ferrule pressing part 30 is attached to the ferrule receiving part 20 by a rotation of a cam, and screw-type a column attachment device 1 in which, for example, the ferrule pressing part 30 is attached to the ferrule receiving part 20 by being screwed into the ferrule receiving part 20.

In the aforementioned embodiments, the description was directed to the configuration in which the ferrule receiving part 20 is provided with the receiving side body 21 and the connecting portion 22. However, it is not limited to such a configuration, and may be a configuration in which the ferrule receiving part 20 is provided with other members, or a configuration in which some of the aforementioned members are not provided.

Further, in the aforementioned embodiments, the description was directed to the configuration in which the ferrule pressing part 30 is provided with the pressing side body 31, the spacer 32, the urging member 33, and the fixture 34. However, it is not limited to such a configuration, and may be a configuration in which the ferrule pressing part 30 is provided with other members, or a configuration in which some of the aforementioned members are not provided.

DESCRIPTION OF SYMBOLS 1 column attachment device
2 column
3 column oven
4 sample introduction part 5 detector
6 carrier gas supply path
7 sample vaporization chamber
8 sample inlet
10 ferrule
20 ferrule receiving part
21 receiving side body
22 connecting portion
30 ferrule pressing part
31 pressing side body
32 spacer
33 urging member
34 fixture
35 pressing plate
36 pressing plate
37 pressing plate
38 operation portion
211 through-hole
212 accommodation recess
213 stepped portion
221 pin
311 first cylindrical portion
312 second cylindrical portion
313 guide hole
314 guide groove
315 introduction groove
316 inclination groove
317 engaging groove
318 inner wall
319 through-hole
321 through-hole
350 displacing mechanism
351 pressing surface
352 shaft portion
353 through-hole
354 operation portion
360 displacing mechanism
361 pressing surface
362 guide portion
363 through-hole
364 through-hole
365 operation portion
370 displacing mechanism
371 pressing surface
372 shaft portion
373 guide hole
374 guide groove
381 guide pin
382 through-hole

The invention claimed is:

1. A column attachment device for attaching a column to an attachment position, comprising:
   a ferrule that is to be attached to the column by being inserted by the column and swaged at one end part side of the ferrule;
   a ferrule receiving part configured to receive the one end part side of the ferrule; and
   a ferrule pressing part configured to be attached to the ferrule receiving part and fix the ferrule by pinching the ferrule between the ferrule pressing part and the ferrule receiving part by pressing the ferrule from the other end part side toward the ferrule receiving part side,
   wherein the ferrule pressing part includes
   a pressing plate configured to press the ferrule, and
   a displacing mechanism configured to displace the pressing plate to thereby switch the pressing plate between a contacting state in which the pressing plate is in contact with the ferrule and a non-contacting state in which the pressing plate is not in contact with the ferrule and the ferrule can pass thorough an inside of the ferrule pressing part.

2. The column attachment device according to claim 1, wherein the ferrule pressing part includes an urging member configured to urge the ferrule toward the ferrule receiving part side via the pressing plate when the pressing plate is in the contacting state.

3. The column attachment device according to claim 1, wherein the displacing mechanism is provided with a shaft portion that rotatably supports the pressing plate, and the pressing plate is switched between the contacting state and the non-contacting state when the pressing plate is rotated centering on the shaft portion.

4. The column attachment device according to claim 3, wherein the displacing mechanism is provided with a plurality of pressing plates, a plurality of shaft portions rotatably supporting each pressing plate, and a rotary plate provided with a plurality of shaft portions, and is configured to switch the pressing plate between the contacting state and the non-contacting state when the rotation plate is rotated to thereby simultaneously rotate the plurality of pressing plates.

5. The column attachment device according to claim 1, wherein the displacing mechanism is provided with a guide portion that slidably holds the pressing plate, and is configured to switch the pressing plate between the contacting state and the non-contacting state when the pressing plate is slid.

* * * * *